US012685440B2

(12) United States Patent
Jolma et al.

(10) Patent No.: US 12,685,440 B2
(45) Date of Patent: Jul. 21, 2026

(54) OPHTHALMIC EXAMINATION APPARATUS AND ALIGNMENT METHOD

(71) Applicant: OPTOMED PLC, Oulu (FI)

(72) Inventors: Ilkka Jolma, Oulu (FI); Ilkka Alasaarela, Kuusamo (FI); Matti Pohjoisaho, Oulu (FI); Juha Lipponen, Oulu (FI); Seppo Rönkkö, Oulu (FI)

(73) Assignee: OPTOMED PLC, Oulu (FI)

( * ) Notice: Subject to any disclaimer, the term of this patent is extended or adjusted under 35 U.S.C. 154(b) by 326 days.

(21) Appl. No.: 18/258,529

(22) PCT Filed: Dec. 15, 2021

(86) PCT No.: PCT/FI2021/050881
§ 371 (c)(1),
(2) Date: Jun. 20, 2023

(87) PCT Pub. No.: WO2022/136730
PCT Pub. Date: Jun. 30, 2022

(65) Prior Publication Data
US 2024/0041322 A1      Feb. 8, 2024

(30) Foreign Application Priority Data

Dec. 21, 2020    (FI) ..................................... 20206352

(51) Int. Cl.
*A61B 3/12* (2006.01)
*A61B 3/14* (2006.01)

(52) U.S. Cl.
CPC . *A61B 3/12* (2013.01); *A61B 3/14* (2013.01)

(58) Field of Classification Search
CPC .. A61B 3/12; A61B 3/14; A61B 3/152; A61B 5/14555; A61B 5/6821
See application file for complete search history.

(56) References Cited

U.S. PATENT DOCUMENTS

| | | | |
|---|---|---|---|
| 6,361,495 B1 | 3/2002 | Grolman | |
| 10,321,822 B1 | 6/2019 | Lee et al. | |

(Continued)

FOREIGN PATENT DOCUMENTS

| | | |
|---|---|---|
| EP | 2949266 A1 | 12/2015 |
| FI | 20185754 A1 | 3/2020 |

(Continued)

OTHER PUBLICATIONS

Dec. 12, 2023 Office Action issued in Finnish Patent Application No. 20206352, pp. 1-7.

(Continued)

*Primary Examiner* — Sharrief I Broome
*Assistant Examiner* — K Muhammad
(74) *Attorney, Agent, or Firm* — Nixon & Vanderhye PC

(57) ABSTRACT

An ophthalmic examination apparatus, characterized in that the ophthalmic examination apparatus comprises at least one visual radiation source and a light manipulation arrangement, which is configured to receive light from the visible radiation source, and form light patterns from the light and direct at least one light pattern of the light patterns in a converging manner toward an pupil aperture in a pupil plane of the ophthalmic examination apparatus and locate the at least one light pattern at a non-zero radial distance from a pupil center of the pupil aperture such that a waist of the light patterns is located at the pupil plane in order to provide a person with guidance for enabling an aperture of an iris of his/her eye to approach and/or locate at the pupil aperture in the pupil plane.

12 Claims, 11 Drawing Sheets

(56)                References Cited

U.S. PATENT DOCUMENTS

| | | | |
|---|---|---|---|
| 2005/0286019 A1 | 12/2005 | Wiltberger et al. | |
| 2009/0002631 A1* | 1/2009 | Campbell | G01B 11/25 |
| | | | 351/212 |
| 2009/0257024 A1* | 10/2009 | Luther | A61B 3/14 |
| | | | 351/221 |
| 2012/0281185 A1 | 11/2012 | Juhasz et al. | |
| 2013/0050649 A1 | 2/2013 | Juhasz et al. | |
| 2013/0128226 A1 | 5/2013 | Yahagi et al. | |
| 2016/0143529 A1 | 5/2016 | Miyashita et al. | |
| 2016/0183788 A1 | 6/2016 | Abramoff et al. | |
| 2016/0302665 A1 | 10/2016 | Swedish et al. | |
| 2016/0374550 A1 | 12/2016 | Stevens et al. | |
| 2018/0220888 A1 | 8/2018 | Tumlinson et al. | |
| 2019/0125184 A1 | 5/2019 | Kramer et al. | |
| 2019/0254514 A1* | 8/2019 | Westphal | A61B 3/102 |
| 2019/0290124 A1* | 9/2019 | Laforest | A61B 3/14 |

FOREIGN PATENT DOCUMENTS

| | | | |
|---|---|---|---|
| GB | 2487873 | A | 8/2012 |
| JP | H03176023 | A | 7/1991 |
| JP | H0614884 | A | 1/1994 |
| JP | 2000037350 | A | 2/2000 |
| WO | 2017025583 | A1 | 2/2017 |

OTHER PUBLICATIONS

International Search Report and Written Opinion of the ISA for PCT/FI2021/050881 dated Mar. 11, 2022, 14 pages.
International Preliminary Report on Patentability for PCT/FI2021/050881 dated Apr. 24, 2023, 41 pages.
Search Report for FI Application No. 20206352 dated Jun. 3, 2021, 2 pages.

* cited by examiner

OPHTHALMIC EXAMINATION APPARATUS AND ALIGNMENT METHOD

CROSS-REFERENCE TO RELATED APPLICATIONS

This application is the U.S. national phase of International Application No. PCT/FI2021/050881 filed Dec. 15, 2021 which designated the U.S. and claims priority to FI patent application No. 20206352 filed Dec. 21, 2020, the entire contents of each of which are hereby incorporated by reference.

FIELD

The invention relates to an ophthalmic examination apparatus and an alignment method.

BACKGROUND

A typical problem with an ophthalmic instrument is how to have alignment between the ophthalmic instrument and an eye that should be examined with the ophthalmic instrument. The problem is particularly challenging for an ophthalmic examination instrument which is used to examine optically portions of eye behind the iris. An example of such an ophthalmic examination instrument is a fundus camera. A wrong alignment between the eye and the fundus camera leads to dim or vignetted images and/or spurious reflections. Challenges in the alignment are caused by the patient and his/her eye movements.

Hence, an improvement would be welcome.

BRIEF DESCRIPTION

The present invention seeks to provide an improvement for the alignment.

The invention is defined by the independent claims. Embodiments are defined in the dependent claims.

LIST OF DRAWINGS

Example embodiments of the present invention are described below, by way of example only, with reference to the accompanying drawings, in which FIG. 1 illustrates an example of an eye and its six degrees of freedom;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may also contain features/structures that have not been specifically mentioned. All combinations of the embodiments are considered possible if their combination does not lead to structural or logical contradiction.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

This document presents an improved solution for finding alignment between an ophthalmic apparatus and an eye that is examined with the ophthalmic apparatus. The ophthalmic apparatus in this document refers to any optical apparatus (for example used for examination or treatment with eye) which requires alignment to the eye. The alignment, in turn, may refer to an adjusting process, which leads to a proper relative position between the eye and the ophthalmic examination apparatus. Additionally, the alignment may also include the proper relative position between the eye and the ophthalmic examination apparatus achieved by the adjusting process.

Figures 1, 2:
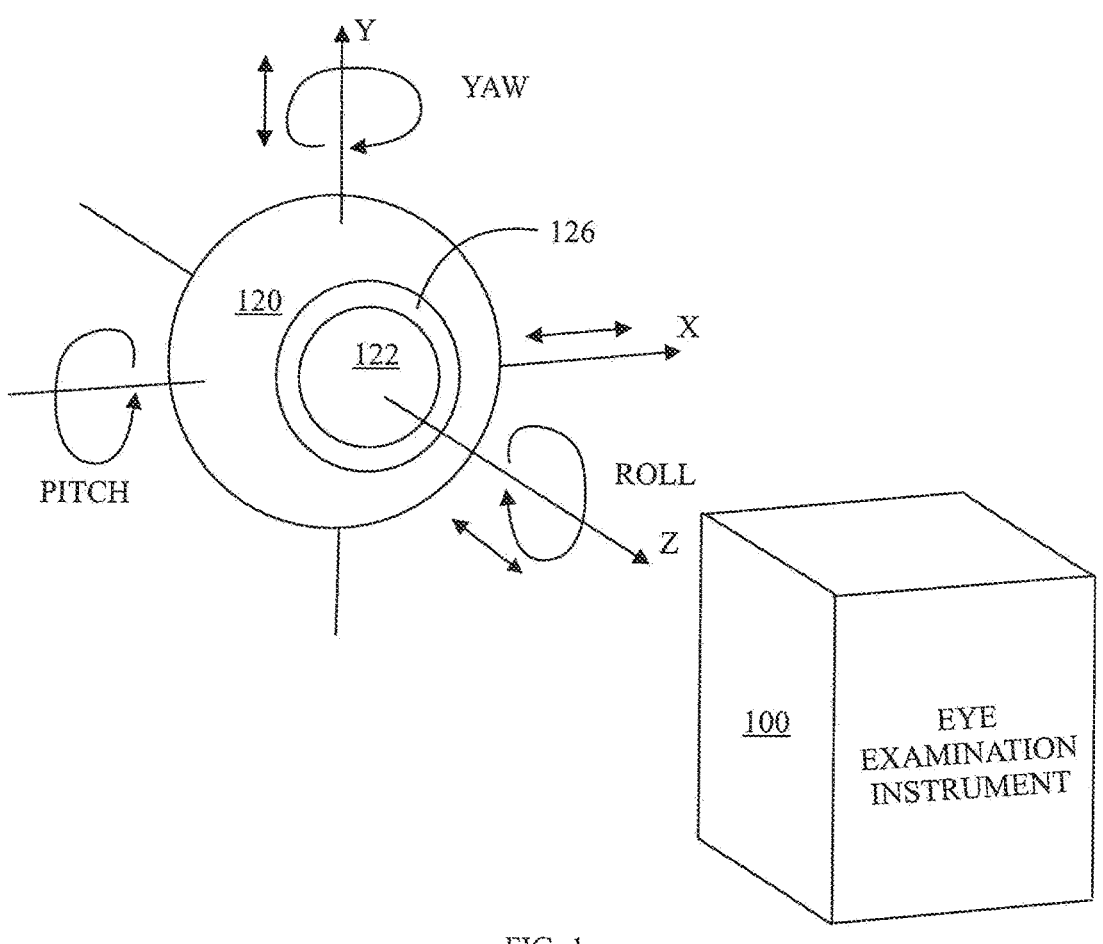
FIG. 2 illustrates an example where an eye is in front of an ophthalmic examination apparatus.

FIG. 1 illustrates an example of an eye 120 and its six degrees of freedom. Namely, the eye 120 may move back and forth along the spatial x-, y- and z-axis. Additionally, the eye 120 may rotate around the x-, y- and z-axis which can be defined in angular coordinates as pitch, yaw and roll. In this example, the x-axis denotes a horizontal axis, y-axis denotes a vertical axis and the z-axis denotes a horizontal axis between the eye 120 and the ophthalmic examination apparatus 100, the x-, y- and z-axes being orthogonal with respect to each other in this example.

In FIG. 1, the eye 120 of a person is in front of the ophthalmic examination apparatus 100. The eye 120 needs to be aligned in certain desired way relative to the ophthalmic examination apparatus 100, which is necessary in order to perform a proper examination with the ophthalmic examination apparatus 100.

Eye alignment means that the eye 120 has been oriented and positioned to match certain values or ranges of these coordinates. The targeted alignment accuracy for each dimension depends on the ophthalmic examination apparatus 100 and the use case.

As shown in FIG. 2, the eye 120 contains a retina 124 and approximately circular iris aperture 122 (see also FIG. 1), whose diameter may vary from a few millimeters up to 10 mm, typically between about 3 mm and about 8 mm, for example.

When the eye 120 is front of the ophthalmic examination apparatus 100, sufficient horizontal and vertical alignments (yaw and pitch) may be obtained such that the ophthalmic examination apparatus 100 generates a fixation target in the person's field-of-view, and the person is instructed to aim his/her eyesight to the fixation target. A fixation target may be arranged such that it guides the eye 120 to a proper yaw and pitch angular alignments.

A proper rotational alignment (roll) may be achieved by the help of the set-up how the person is positioned in respect to the ophthalmic examination apparatus 100 as a whole. For example, if the person is standing or sitting, the roll-angle of the eye 120 may be known with sufficient accuracy and the ophthalmic examination apparatus 100 may be aligned accordingly. For further adjustment, the roll-angle, the ophthalmic examination apparatus 100 may also generate a target figure in the person's field-of-view, and the person is instructed to rotate his/her head so that the target figure is in a desired rotation position.

For achieving a proper spatial xyz-alignment, the ophthalmic examination apparatus 100 can generate an alignment image to the person's field-of-view, which is taught in this document. The visibility of certain parts of the alignment image can be made to change when the eye 120 is placed in different positions in the environment of the desired position, and the person can be instructed to move his/her head with respect to the instrument optics such that a certain or desired visibility condition is fulfilled.

Instead of a typical alignment work made by the operator of the ophthalmic examination apparatus 100, this alignment arrangement allows the person alone to perform the precise alignment between the eye 120 and the ophthalmic examination apparatus 100. Of course, the operator may also help the person in this alignment process but even in that case the alignment is simple and gives information to perform the alignment in a self-steering manner. This alignment is now described in more detail.

Assume now that FIG. 2 illustrates a situation where the eye 120 is positioned at a desired ideal position with respect to the ophthalmic examination instrument 100. An eye axis EA goes through a center PO of an iris 126 of the eye 120 and a field center FO in a field plane FP. A pupil plane PP coincides at the center PO of the eye 120 at least approximately parallel to and at least approximately at the same plane as an aperture 122 of an iris 126 of the eye 120. Let us define eye axis EA as line perpendicular to the pupil plane which crosses pupil plane at PO. Because eye 120 and the ophthalmic examination instrument 100 are in a proper position with respect to each other in this example, the aperture 122 of the eye 120 is at the same place as the pupil aperture 110 of the ophthalmic examination apparatus 100 in the pupil plane PP of the ophthalmic examination apparatus 100. The pupil aperture 110 is an area in the pupil plane PP and the area of the pupil aperture 110 and thus the pupil aperture 110, per se, is optically limited and also defined by the ophthalmic examination apparatus 100.

The field plane FP is a distant plane, which may locate about 1 m to about infinity from the ophthalmic examination instrument 100. The field plane FP is parallel to the pupil plane PP and it is on the same side with respect to the pupil plane PP as the retina 124 of the eye 120. A crossing point of the eye axis EA and the field plane FP is called as the field center FO. A position on the field plane FP may be defined in angular coordinates around the pupil center PO.

The arrows in FIG. 2 illustrate rays or beams of light from a light manipulation arrangement 104 of the ophthalmic examination apparatus 100.

In more detail, the ophthalmic examination apparatus 100 comprises in addition to the light manipulation arrangement 104 at least one visual radiation source 102. The light manipulation arrangement 104 receives light from the visible radiation source 102, and forms light patterns 106 from the light (see the dashed arrow that does not go through the aperture 122 of the iris 126 nor the pupil aperture 110 and the arrows that do go through the aperture 122 of the iris 126 and the pupil aperture 110). The light manipulation arrangement 104 directs at least one light pattern 108 of the light patterns 106 in a converging manner toward the pupil aperture 110 of the ophthalmic examination apparatus 100 (see the arrows that go through the aperture 122 of the iris 126 and the pupil aperture 110). Some of the light patterns 108 may be diverging before and/or after the pupil plane PP (see FIG. 14). The pupil aperture 110, which is a non-structural object, is formed or determined by the optics of the ophthalmic examination apparatus 100. Its location, size and shape depends a little bit on the eye 120 that is examined. However, the effect of the eye 120 that is examined may be taken into account during the design and manufacturing phase of the ophthalmic examination apparatus 100 such that a standard eye model is utilized.

The standard eye may be based on an Emsley model, Emsley-Gullstrand model, or Liou and Brennan schematic eye model, for example. The eye model may be similar to an anatomical and optical eye. It may have a power of about 60.4 D and an axial length of about 24 mm for example. The eye model may estimate aberrations in a visible range of light. The eye model used in the the ophthalmic examination apparatus 100 during an examination may have variation depending on a size of a person 160 that is examined, sex and age especially when it is a question of a child, for example. That is, a model may be selected based on anatomical and/or optical information on the person 160 to be examined.

The at least one light pattern 108 passes through and is it within the pupil aperture 110 of the ophthalmic examination apparatus 100. In this manner, a waist W of the at least one light pattern 108 is located at the pupil plane PP (see also FIG. 14). The at least one light pattern of the light patterns 106, which does not belong to the at least one light pattern 108 that passes through the pupil aperture 110, may be directed to the pupil plane PP in a converging or diverging manner. When a light pattern 108 is directed toward the pupil plane PP in converging manner, a shortest distance between the eye axis EA and the light pattern 108 is between the field plane FP and the ophthalmic examination instrument 100. In other words, the shortest distance between the eye axis EA and the light pattern 108 is not in the field plane FP or at the ophthalmic examination instrument 100.

The light manipulation arrangement 104 locates the at least one light pattern 108 at a non-zero radial distance from the pupil center PO of the pupil aperture 110 in the pupil plane PP of the ophthalmic examination apparatus 100. In an embodiment, the at least one light pattern 108 may be closer to the outer border of the pupil aperture 110 than the pupil center PO of the pupil aperture 110.

This kind of arrangement provides a person with guidance for enabling the aperture 122 of the iris 126 of his/her eye 120 to approach the pupil aperture 110 in the pupil plane PP and/or to locate the aperture 122 of the iris 126 of his/her eye 120 at the pupil aperture 110 in the pupil plane PP. Both of the approaching and the location are based on maximization of the at least one light pattern 108 seen by the person with the eye 120. The aperture 122 of the iris 126 of his/her eye 120 will be aligned with the pupil aperture 110 of the ophthalmic examination apparatus 100, which allows the person to see the at least one light pattern 108 either fully from a geometric point of view or with a maximum brightness.

In an embodiment, the light patterns 106 and the at least one light pattern 108 of the light patterns 106 may be made of visible light or a combination of visible light and lack of visible light. That is, the light patterns 106 may include at least one area of made of visible light and at least one area made of lack of visible.

In an embodiment, the light patterns 106 and the at least one light pattern 108 of the light patterns 106 may be made of at least one contrast between intensity of the visible light. Then the light patterns 106 and the at least one light pattern 108 of the light patterns 106 may include at least one area of made of one intensity of visible light and at least one area made of another intensity of visible light.

In an embodiment, the light patterns 106 and the at least one light pattern 108 of the light patterns 106 may be made of at least two different colors. Then the light patterns 106 and the at least one light pattern 108 of the light patterns 106 may include at least one area of made of one color of visible light and at least one area made of another color of visible light.

When the eye 120 is roughly brought to the working position of the ophthalmic examination apparatus 100, one or more of the at least one light pattern 108 that is directed to the pupil aperture 110 may at least partially pass the aperture 122 of the iris 126 of the eye 120, and form visible illuminated area at retina 124. That is the person will see an illuminated area in his/her field-of-view. The retina 124 may be at least approximately an optical conjugate to the field plane FP such that the irradiance distribution on the retina 124 may at least roughly resemble to the irradiance pattern at the field plane FP.

Figure 3:
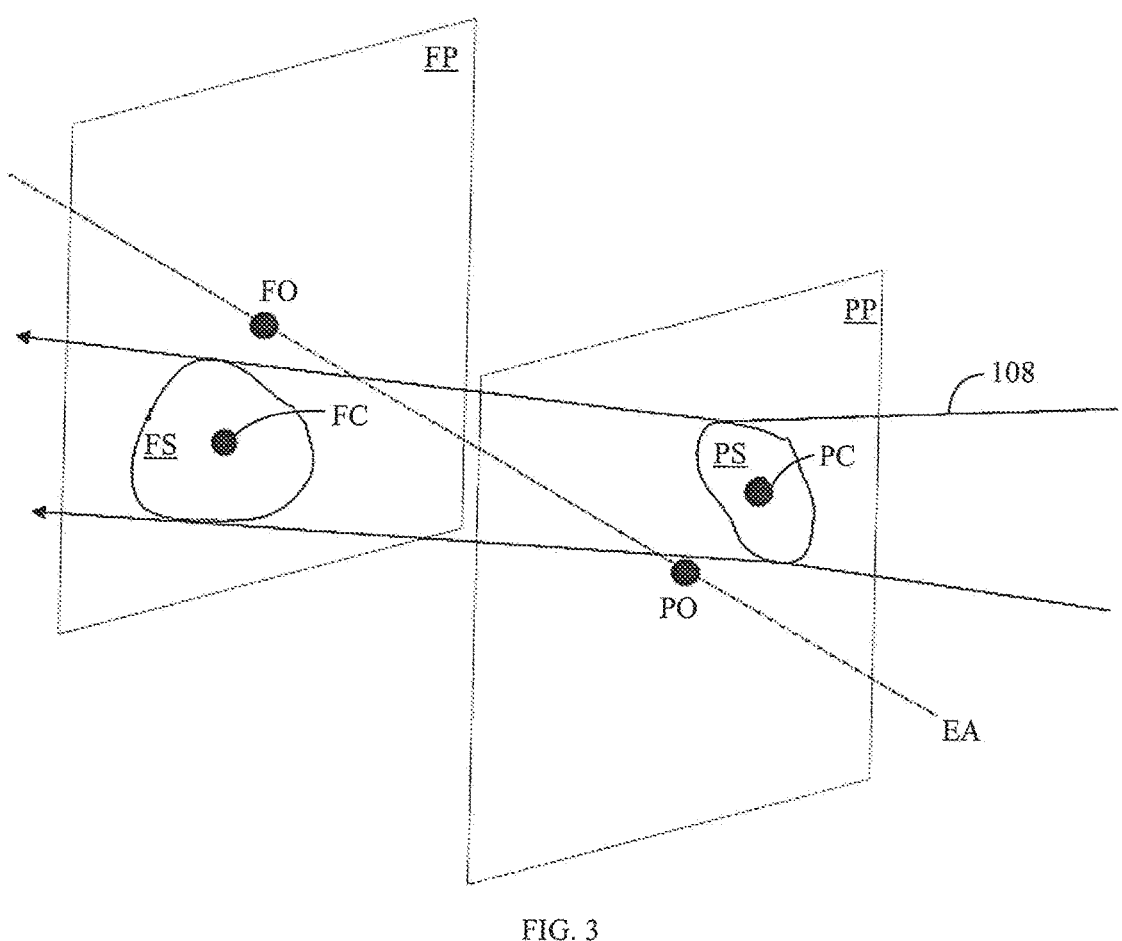
FIGS. 3 and 4 illustrate examples of at least one light pattern as beams and their cross sections in the pupil plane.

In an example illustrated in FIG. 3, one beam that may represent one of the at least one light pattern 108 is directed toward the pupil plane PP and the field plane FP. In an example illustrated in FIG. 4, two beams or rays that may represent one of the at least one light pattern 108 are directed toward the pupil plane PP and the field plane FP.

Figure 4:
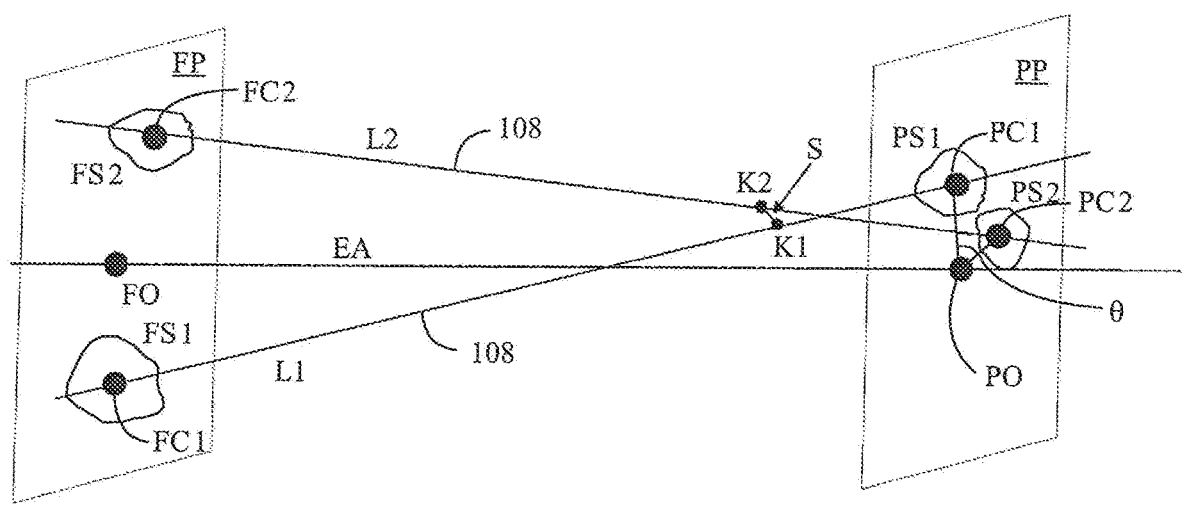

In an embodiment an example of which is illustrated in FIGS. 3 and 4, irradiance of any of the at least one light pattern 108 that is brighter than its environment, may be concentrated inside a subarea PS, PS1, PS2, which may locate between about 1 and about 6 mm or between about 0.5 and about 10 mm distance from the pupil center PO, within a sector in the pupil plane PP. In a corresponding manner, different light patterns 108, which are visibly less bright than the environment next to them, may be concentrated inside a subarea PS of a sector in an embodiment.

In an embodiment, irradiance of one or more of the at least one light pattern 108 in the field plane FP may be concentrated inside a region FS, FS1, FS2, which is located inside a cone, whose peak is at PO, axis parallel to eye axis EA towards the FP, and half-angle $\theta=60°$.

In an embodiment, irradiance distribution of each of the at least one light pattern 108 in the pupil plane PP and the field plane FP may have centroid at locations called a pupil centroid PC and a field centroid FC, respectively.

FIG. 4 illustrates an example where two beams or rays have centroids PC1, PC2 and as FC1, FC2 in the pupil plane and the field plane FP, respectively. One of the beams or rays belong to a first light pattern of the at least one light pattern 108 and another of the beams or rays belong a second light pattern of the at least one light pattern 108. Lines L1 and L2 go between PC1, FC1 and PC2, FC2, respectively. Let S be the shortest distance between the lines L1 and L2. The shortest distance is between points K1 and K2 at lines L1 and L2, respectively.

In an example of FIG. 4, individual beams of the at least two light patterns 108 have pairwise distinct subareas PS1 and PS2 and/or distinct regions FS1 and FS2 in the pupil plane PP and the field plane FP, respectively.

Now, if both K1 and K2 are located on the same side as the field plane FP with respect to the pupil plane PP, as shown in the FIG. 4, the pair of the beams or rays of the light patterns 108 may be said to have positive (+) angle. The value of the angle is between the lines L1 and L2. If both of the points K1 and K2 locate on the same side as the ophthalmic examination apparatus 100 with respect to the pupil plane PP, the pair may be said to have a negative (−) angle. In an embodiment, an angle between the light patterns 108 may be equal or smaller than −10° or equal or larger than 10° angle. The condition can be used as a minimum condition for Z+ or Z− alignment in the Z-axis.

In an embodiment, an angle between the light patterns 108 may be equal to or smaller than −10°, and another angle between the light patterns 108 may be equal or larger than 10°. This condition may be used as a minimum condition for Z-alignment in both directions in the Z-axis.

In an embodiment, an angle between the light patterns 108 may be equal or smaller than −10°, and an angle of one or more of the at least one light pattern 108 may be equal to or larger than 10° with respect to the eye axis EA.

With at least one such pair of the light patterns 108 the centroids PC1 and PC2 may be separated at least by 100° angle θ on the pupil plane PP when viewed from the pupil aperture PO in an embodiment. This condition may be used as a minimum condition for alignment in one dimension in the PP-plane (such as X- or Y- dimensions, for example).

With at least two such pairs of the light patterns 108 the centroids PC1 and PC2 may be separated at least by 100° angle when viewed from PO (which may comprise partially same alignment beams). This may be used as a minimum condition for alignment in two dimensions in the PP-plane.

It should be noted that the at least one light pattern 108 may have a sharp edge but it may also be so that the at least one light pattern 108 does not have a sharp edge but it may have a smooth edge. The at least one light pattern 108 may also have a long tail (due to stray light, for example).

Figure 7:
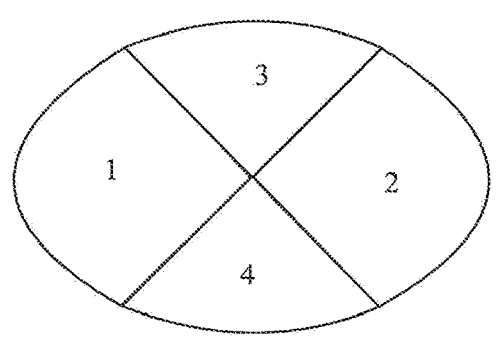
FIG. 7 illustrates an example of four sectors each having a light pattern such that all light patterns pass through an aperture of an iris of an eye.

A common envelope 700 of the light patterns 106, an example of which using only the light patterns 108 that are directed though the pupil aperture 110 is illustrated in FIG. 7, can be defined from the set of light patterns 106 as follows:

the light patterns 106 or 108 can be split at the pupil plane PP a front side 702 of the common envelope 700 is a volume between the pupil PP and the ophthalmic examination apparatus 100. The front side 702 of the common envelope 700 is enclosed in each plane parallel to pupil plane PP by a convex hull containing the cross-sections of the light patterns 106 a back side 704 of the common envelope 700 is a volume between the pupil plane PP and the field plane FP. The back side 704 is enclosed in each plane parallel to the pupil plane PP by a convex hull containing the cross-sections of the light patterns 106.

Although FIG. 7 illustrates only the common envelope 700 for the light patterns 108 that are directed through the pupil aperture 110, the same applies to all light patterns 106. In an embodiment, the light patterns 106 contain only the light patterns 108 that are directed toward and through the pupil aperture 110 in a converging manner.

The convex hull can be approximately determined by defining the edges of the light patterns 106 or 108 by using a threshold value for total power for each light pattern 106 or 108 such that in each plane parallel to the pupil plane PP, the light patterns 106 or 108 is bounded by an equal-irradiance curve which encloses the total power of the light patterns 106 or 108 determined by the threshold value. So, the common envelope 700 is function of this threshold value. The common envelope 700 may contain approximately 50%-90% of a total power of the light patterns 106 or 108, for example. Correspondingly, an envelope of a single light pattern 106 or 108 may contain approximately 50%-90% of a total power of said single light pattern 106 or 108, for example.

In an embodiment examples of which are illustrated in FIGS. 5 to 10, irradiance of different light patterns 108, which are visibly brighter than the environment next to them, may be in different sectors around the pupil center PO. In an embodiment, an opening angle of the sectors may be equal to or less than 10°, for example. In an embodiment, an opening angle of the sectors may be equal to or less than 25°, for example. In an embodiment, an opening angle of the sectors may be equal to or less than 50°, for example. In an embodiment, an opening angle of the sectors may be equal to or less than 90°, for example. In an embodiment, an opening angle of the sectors may be equal to or less than 180°, for example. In an embodiment, most of optical power of the visible light of each of the at least one light pattern 108 locates inside the sector. In FIGS. 5 to 10 there are four sectors but the proposed solution is not limited to the number.

In a corresponding manner, different light patterns 108, which are visibly less bright than the environment next to them, may be in different sectors around the pupil center PO in an embodiment.

Figure 5:
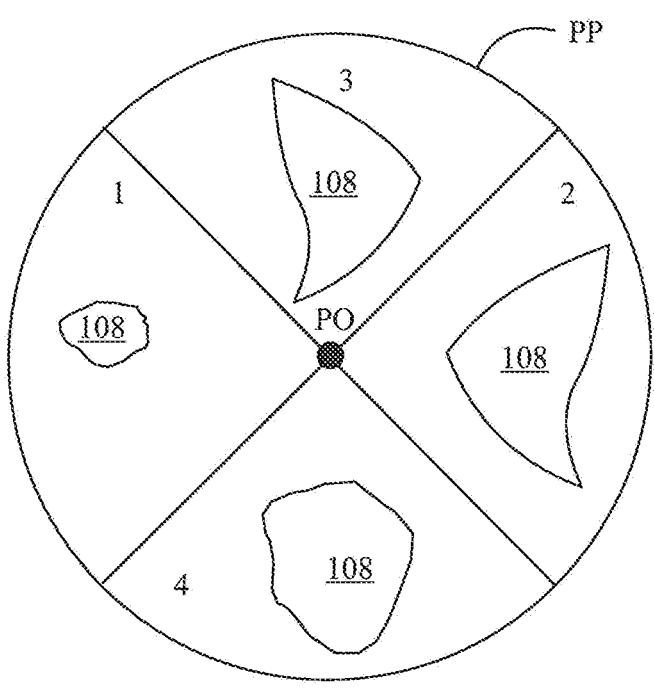
FIG. 5 illustrates an example of light patterns and their sectors in the pupil plane.

FIG. 5 illustrates a set of four sectors 1, 2, 3 and 4 related to different light patterns 108 in the pupil plane PP. Each of the sectors 1 to 4 may have a light pattern 108 that is directed through the pupil aperture 110 of the pupil plane PP in a converging manner. The light pattern 108 in each of the sector 1 to 4 may be a single beam of light, a plurality of beams of light or a part of a common figure of all the sectors 1 to 4 (see FIG. 11). The envelope of the set of the converging light beams 108 has a waist W approximately at the pupil plane PP (see also FIG. 14).

Figure 6:
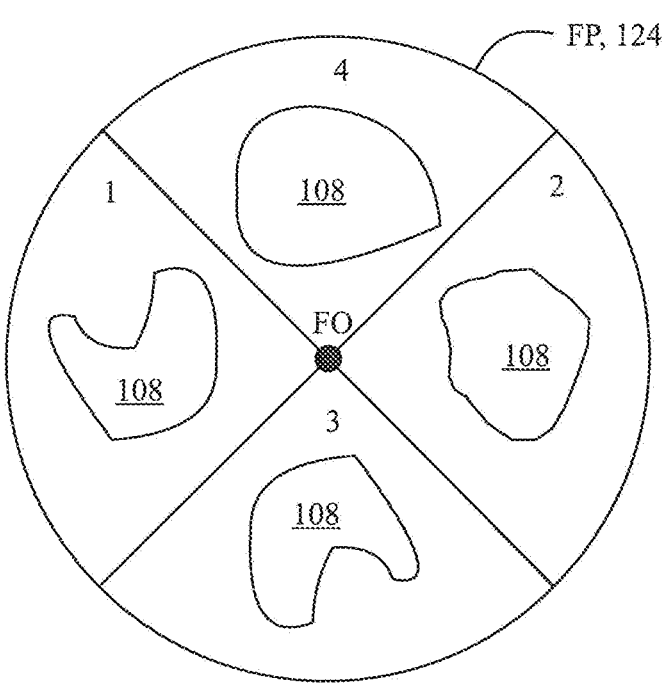
FIG. 6 illustrates an example of light patterns and their sectors in the field plane.

FIG. 6 shows a cross-sections of the light patterns 108 in the field plane FP and at least approximate on the retina 124. Because of the different directions of the light patterns 108 in different sectors 1 to 4, the light pattern that hits the upper sector in the pupil plane PP hits a lower sector in the field plane FP in this example. That is why the numbering of sectors changes in FIGS. 5 and 6.

FIG. 7 illustrates a situation where the eye 120 and the ophthalmic examination apparatus 100 are aligned in a desired manner. Then all sectors 1 to 4 can be seen by the eye 120, i.e. the iris 126 of the eye 120 does not block the light patterns 108 that are directed through the pupil aperture 110 in a converging manner. That is why, all sectors 10 to 4 are illustrated as white.

Figure 8:
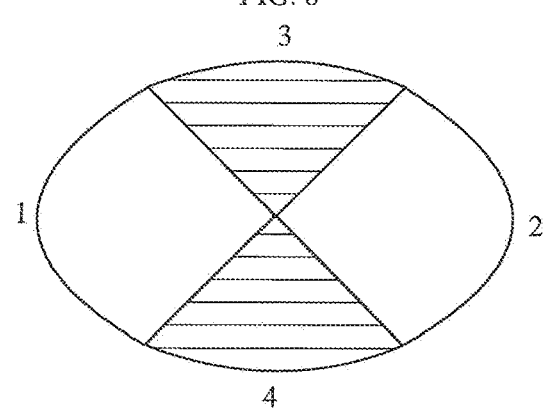
FIG. 8 illustrates an example of the four sectors each having a light pattern such that patterns in sectors 1 and 2 do not pass through an aperture of an iris of an eye.

FIG. 8 illustrates a situation where a distance between the eye 120 and the ophthalmic examination apparatus 100 is too short, i.e. the ophthalmic examination apparatus 100 is too close to the eye 120. Because of the chosen directions of the light patterns 108 in this example, the iris 126 of the eye 120 starts blocking the light patterns 108 of the sectors 1 and 2, and they are marked with hatch filling.

Figure 9:
FIG. 9 illustrates an example of the four sectors each having a light pattern such that patterns in sectors 3 and 4 do not pass through an aperture of an iris of an eye.

FIG. 9 illustrates a situation where a distance between the eye 120 and the ophthalmic examination apparatus 100 is too long, i.e. the ophthalmic examination apparatus 100 is too far from the eye 120. Because of the chosen directions of the light patterns 108 in this example, the iris 126 of the eye 120 starts blocking the light patterns 108 of the sectors 3 and 4, and they are marked with hatch filling.

Figure 10:
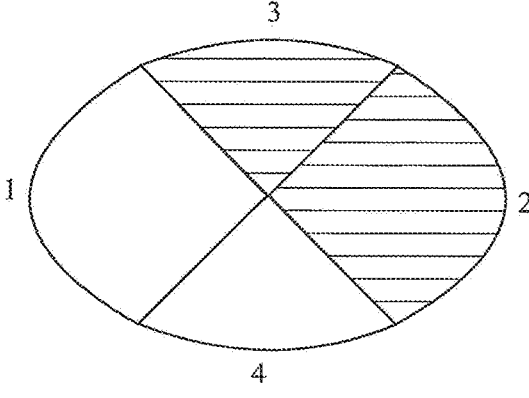
FIG. 10 illustrates an example of the four sectors each having a light pattern such that patterns in sectors 2 and 3 do not pass through an aperture of an iris of an eye.

FIG. 10 illustrates a situation where the eye 120 and the ophthalmic examination apparatus 100 have a lateral shift in the x-direction, i.e. the ophthalmic examination apparatus 100 and the eye 120 have moved sideward from the optimal position. Because of the chosen directions of the light patterns 108 in this example, the iris 126 of the eye 120 starts blocking the light patterns 108 of the sectors 1 and 4, and they are marked with hatch filling. Correspondingly, an opposite deviation from the optimal position in the x-direction would cause sectors 2 and 4 to be blocked by the iris 126. In a similar manner, a deviation from the optimal position in the y-direction would cause sectors 2 and 3 to be blocked by the iris 126, and an opposite deviation in the y-direction would cause sectors 1 and 3 to be blocked by the iris 126. FIGS. 7 to 10 illustrate examples of possibilities. A person skilled in the art can find different directions for the light patterns 108 which correspondingly result in different blocking of sector at the iris 126. The number of sectors in the examples of FIGS. 7 to 10 is four. However, the solution is not limited to that number. The inventors and the applicant have found by testing, that a person will easily be able to align his/her eye 120 by using these kind of cues.

Figures 11, 12A, 12B:
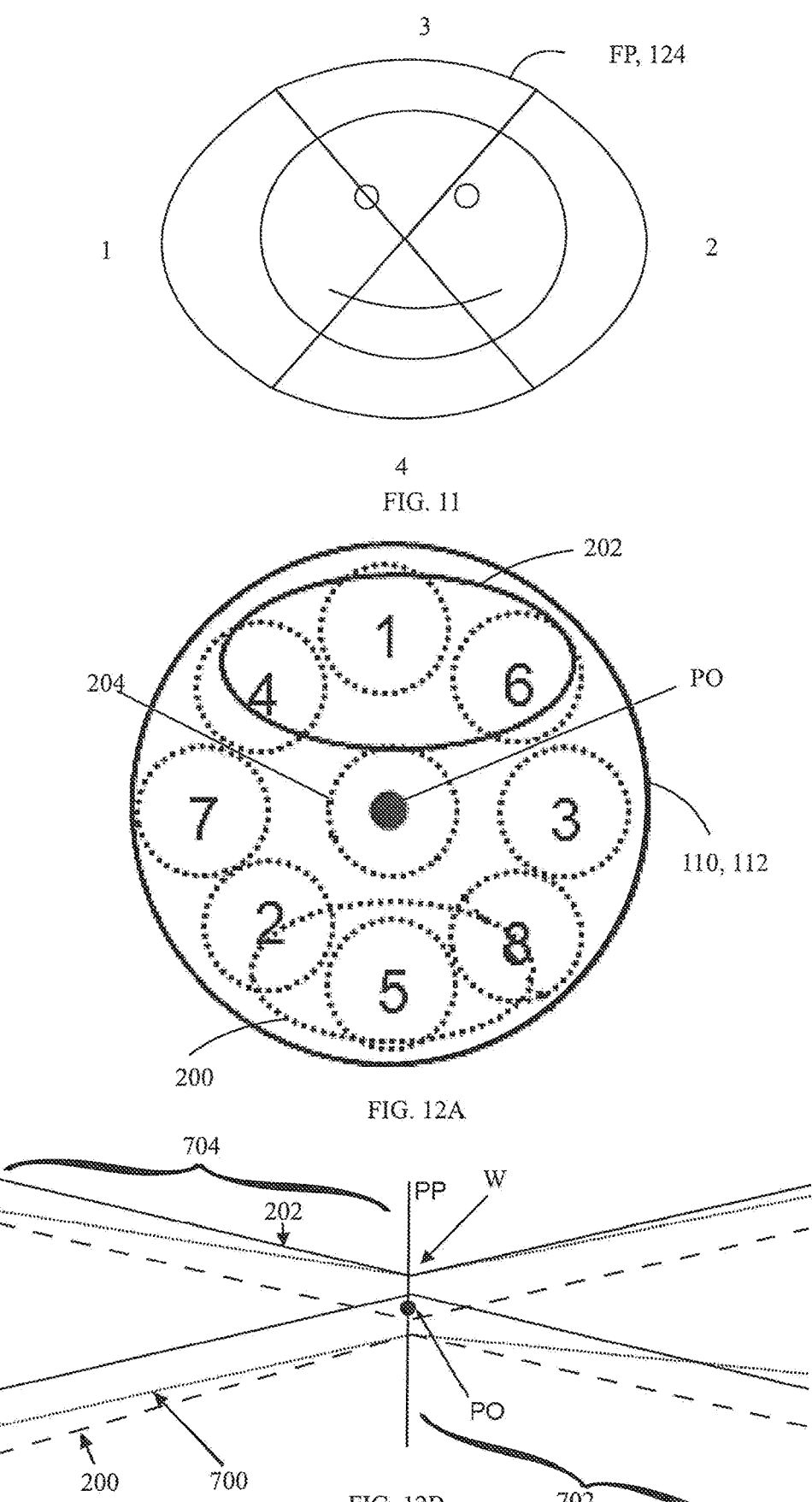
FIG. 11 illustrates an example where the light patterns form a recognizable figure.
FIG. 12A illustrates an example of a distribution light patterns, an illuminating beam and an imaging beam in a pupil aperture and/or an aperture of an iris located at a pupil plane.
FIG. 12B illustrates an example of beams of light patterns, illuminating beam and imaging beam through a pupil aperture.

FIG. 11 illustrates an example of an embodiment, where light patterns 108 of different sectors 1 to 4 together form a recognizable figure such as a face in the field plane FP and on the retina 124 when the light patterns 108 that that are directed toward the pupil aperture 110 in a converging manner pass properly through the aperture 122 of the iris 126.

The recognizable figure, such as that illustrated in FIG. 11, may be formed using a field stop in conjunction of the at least one visual radiation source 102. A field stop is an aperture or any component which structures the light to the form which imaged to the field plane FP forms the needed irradiance distribution in the field plane FP.

A field stop may form irradiance distribution to an image, which is then imaged to the field plane FP, i.e. at least approximately to the person's retina 124. Referring again to FIGS. 7 to 10 and FIG. 11, the four irradiance distributions of the light pattern 108 in the sectors 1 to 4, may each contain a sub-image as light patterns 108. The sub-images may form together one larger image as shown in FIG. 11. The target of the alignment process for the person becomes a task to move his/her head and the eye 120 such that the image in general and in this example the face becomes maximally visible.

In a field stop component, the image such as the face in FIG. 11 for the alignment may be formed by using a micro-display illuminated by the light from the light source 102. The image for the alignment may be formed by using a modulator which modulates the beam of light according to the content of the image. The modulator may comprise an illuminated spatial or angular modulator such as liquid-crystal display (LCD), liquid-crystal on silicon (LCOS), digital micro-mirror device (DMD), acousto-optical modulator (AOM), scanning micro-electro-mechanical-system (MEMS), scanning mirror, or diffractive projection engine such as HOLOEYE. The image for the alignment may also be formed by a matrix of separate light sources, such as array of light emitting diodes (LED), or organic-light-emitting display. The image for alignment may also be formed by at least partially transparent aperture or slide, which is illuminated by at least one light source.

The image for alignment may be varied. By that way, such an image may be used which works well with each person that is examined. For example, when a person is a child, the used image may be different from a working image of an adult, for example.

In more general terms, any irradiance distribution, which the light pattern(s) 108 may form in the field plane FP, may also be referred to as the image for alignment.

FIG. 12A illustrates an example of light patterns 108 that are output in a converging manner and that are in a form of beams of light at the pupil plane PP. The largest circle in FIG. 12A is the the pupil aperture 110 of the ophthalmic examination apparatus 100 or the aperture 122 of the iris 126. Because the beams of light of the light patterns 108 are in different sectors, they are numbered here 1, 2, 3, 4, 5, 6, 7 and 8. The ophthalmic examination instrument 100 may also direct an illumination beam 200 to the eye 120. Additionally, that the ophthalmic examination instrument 100 may imagine the eye 120 through an imaging beam 202. Based on the Gullstrand's principle, the illumination beam 200 and the imaging beam 202 do not overlap at the pupil plane PP. Furthermore, the ophthalmic examination instrument 100 may direct a beam 204 of a fixation target to the eye 120. In the pupil plane PP, it may be blurred or obscure although it may also be a well collimated beam.

FIG. 12B shows an example of a side view of the imaging beam 202, illumination beam 200 and the envelope beam 700 of the set of light patterns 108 that are directed through the pupil aperture 110 around the pupil plane PP. The imaging beam 202, the illumination beam 200, and the envelope beam 700 may have a common waist W at the pupil plane PP. The illumination and imaging beams 200, 202 may be substantially inside the envelope beam 700 at the pupil plane PP. By this way, when the eye 120 is displaced from its desired position such that it causes vignetting to illumination and/or imaging beams 200, 202, it will show up to the person as dimming or fainting one or more light patterns 108 that are directed through the pupil aperture 110, which gives cue to the person how he/she needs to align his/her eye 120.

Figures 13, 14:
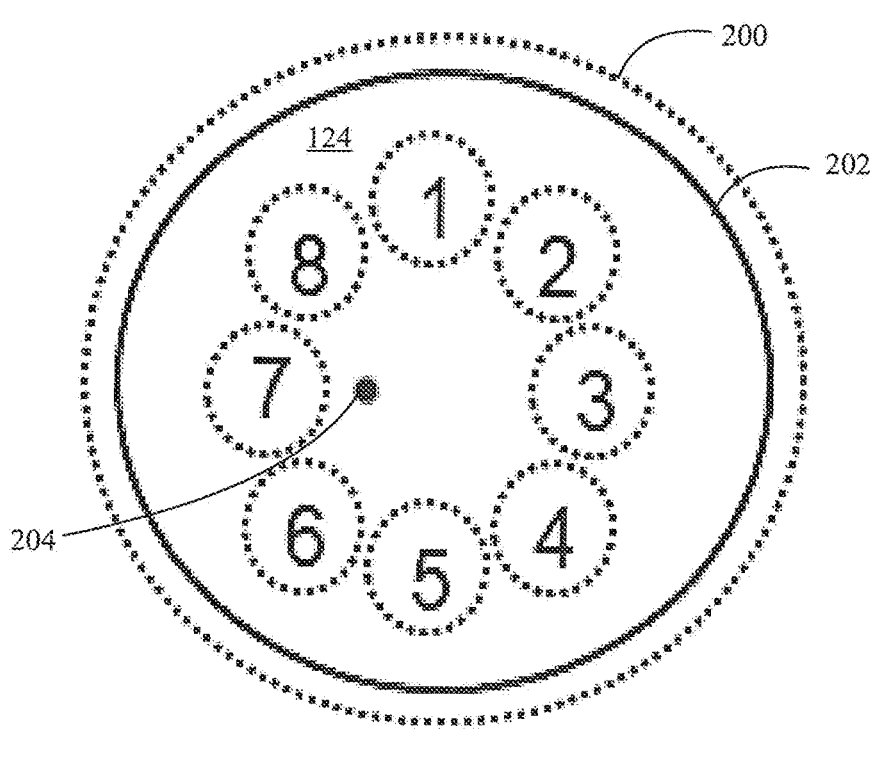
FIG. 13 illustrates an example of a distribution light patterns, an illuminating beam and an imaging beam in a pupil aperture on a retina.
FIG. 14 illustrates an example of beams of light patterns through a pupil aperture of a pupil.

FIG. 13 illustrates an example of the light patterns 108 of FIG. 12A on the retina 126. The illumination beam 200 covers a large area of the retina 124, which is also covered by the imaging beam 202. In that manner, an image or a video may be captured of the retina 124. Figure also illustrates the spot of the beam 204 of the fixation target on the retina 124. The fixation target guides the eye 120 to gaze toward it such that a desired area of the eye 120 can be examined with the ophthalmic examination instrument 100.

Spatial alignment of the eye 120 to the light patterns 108 can be done by the person by the help of a set of eight light patterns 108 in this example. When the person can see all the eight light patterns 108 properly, his/her eye 120 is at a position which allows a proper examination of his/her eye 120.

FIG. 14 illustrates an example how the light patterns 108 may be directed through the pupil aperture 110. The light patterns 108 may also be directed through the aperture 122 of the iris 126 in a corresponding manner when the aperture 122 of the iris 126 and pupil aperture 110 overlap in the pupil plane PP. In this example the light patterns 108 are illustrated as collimated beams of light. In this example a number of the beams of light is 8 without limiting to it. As can be seen in FIG. 14, the waist W of the light patterns 108 is at the pupil plane PP. The waist W is about the same size as the pupil aperture 110. The envelope 700 is the outer surface of the volume within which the light patterns 108 that pass through the pupil aperture 110 are.

FIGS. 15, 16, 17 and 18 show examples of a person's view i.e. light spots on the retina 124 during an exemplary alignment process by using the set of light patterns 108 that pass through the pupil aperture 110 and that are the same as in FIGS. 12A to 14.

Figure 15:
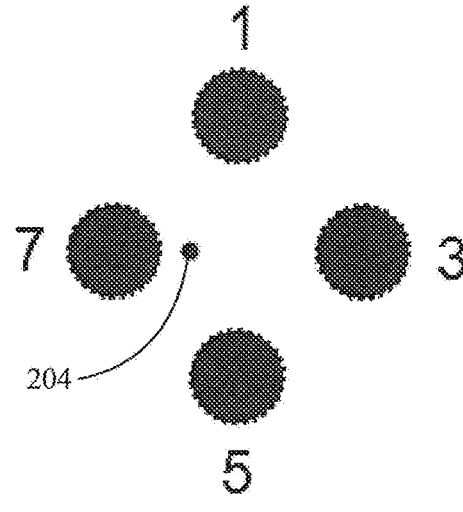
FIG. 15 illustrates an example of spots of beams of light patterns on a retina when an eye is too far from the ophthalmic examination apparatus.
Figure 16:
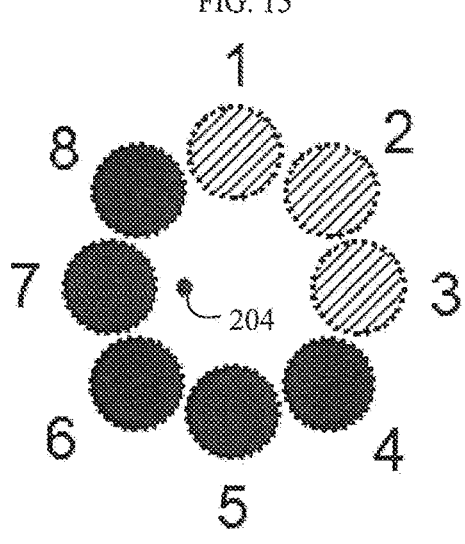
FIG. 16 illustrates an example of spots of beams of light patterns on a retina when an eye is offset sideways with respect to the ophthalmic examination apparatus.
Figure 17:
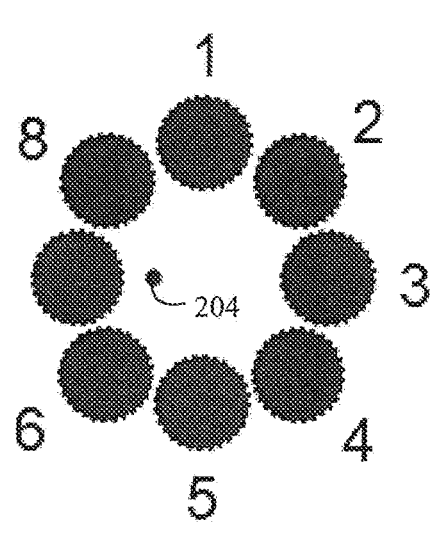
FIG. 17 illustrates an example of spots of beams of light patterns on retina when an eye is at a correct position with respect to the ophthalmic examination apparatus.
Figure 18:
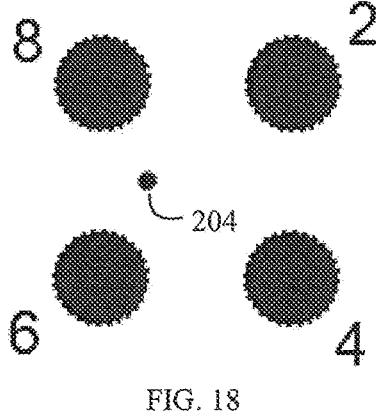
FIG. 18 illustrates an example of spots of beams of light patterns on a retina when an eye is too close the ophthalmic examination apparatus.

When the ophthalmic examination instrument 100 is brought approximately to a working position, but yet too far from the eye 120, the person will see the fixation target 204 and light patterns 108 of sectors 1, 3, 5, 7, as shown in FIG. 15. The person fixates his eyesight towards the fixation spot 204 and starts searching eye position where all the light patterns 108 that are directed through the pupil aperture 110 in the sectors 1, 2, 3, 4, 5, 6, 7 and 8 are visible. Soon he/she finds out that light patterns 108 in some sectors will disappear if he/she moves the eye 120 sideways. When the person brings his/her eye 120 closer to the ophthalmic examination instrument 100, while keeping the eye 120 centered in a correct position, until he/she finds, as depicted in FIG. 16, that the light patterns 108 of all sectors 1 to 8 are visible, however light patterns 108 in three sectors are dim/faint. He/she adjusts the eye position in a diagonal direction such that all the light patterns 108 of all sectors 1 to 8 are visible, as shown in FIG. 17. The person may trigger the ophthalmic examination instrument 100 to capture an image of his/her eye 120 at that position. FIG. 18 shows still another view, where the eye 120 is brought too close to the ophthalmic examination instrument 100 which cases loss of visibility of some of light patterns 108 in some sectors.

Figure 19:
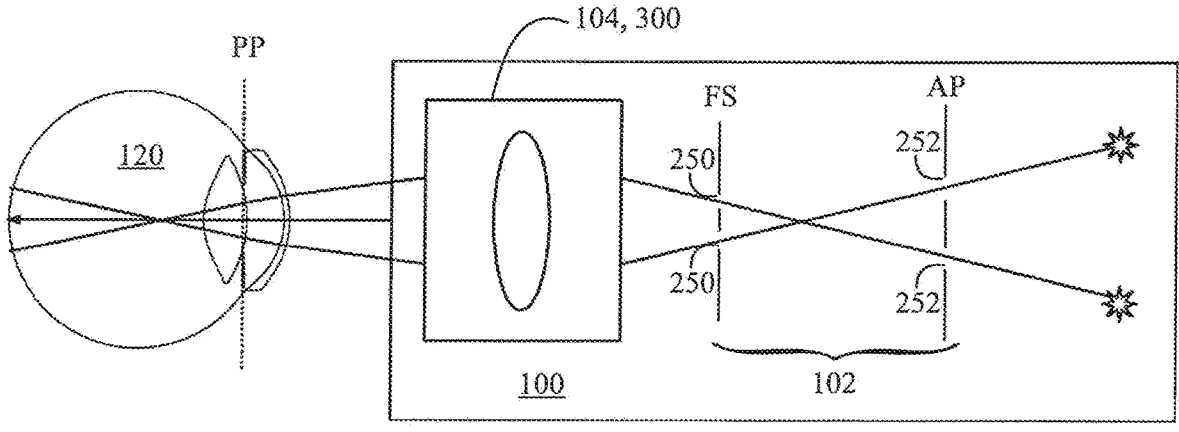
FIG. 19 illustrates an example of a light manipulation arrangement, which comprises at least one image forming optical component.

In some embodiments an of which is shown in FIGS. 19, the light manipulation arrangement 104 comprises at least one image forming optical component 300, which forms an image of an aperture plane AP of the at least one visual radiation source 102 in the pupil plane PP. The aperture plane AP creates in this example the light patterns 106. In an embodiment, the aperture plane AP comprises the light patterns 108 that are directed through the to to the pupil aperture 110 in a pupil plane PP.

The at least one image forming optical component 300 may comprise one of more optically refractive and/or reflective components which may form a real image or a virtual image. The one of more optically refractive and/or reflective components may comprise at least one lens and/or mirror, which has a curved surface.

In more detail, FIG. 19 illustrates an example of the ophthalmic examination instrument 100 which may be used to form a set of the light patterns 108 described in association with FIG. 12A to 18, although for clarity the example of FIG. 19 is described only with two beams which represent the light patterns 108 that pass the pupil aperture 110. The sketched ophthalmic examination instrument 100 comprises two optical radiation sources 102 that has two apertures 250, 252 one after another for each of the light patterns 108 for forming the two beams, and the light manipulation arrangement 104, 300. The two light patterns 108 are represented by two rays, originating from the two optical radiation sources 102, passing through the two apertures 250, 252, towards the image forming unit 300, which further guides the beams to the pupil plane PP. The image forming unit 300 images the apertures 252 to the pupil plane PP, and forms in this manner the needed irradiance distribution of the light patterns 108 at the pupil plane PP. The image forming unit 300 may further image other apertures 250 to the field plane FP. This ensures that the irradiance distribution of the light patterns 108 is desirable in the field plane FP in which case they can be called illumination field stops FS. The line with arrow depicts a ray from a fixation target potentially generated by the ophthalmic examination instrument 100. Now, when the ophthalmic examination instrument 100 is brought roughly in its operating position relative to the eye 120, the fixation target guides the eye 120 to the desired gaze direction, and the light patterns 108 become at least partially visible to the person's eye 120, and so the person is capable of performing the more precise alignment of the eye 120 to the ophthalmic examination instrument 100.

The image forming optics of the light manipulation arrangement 104, 300 may comprise any optical system which is capable of forming at least a rough image of the aperture plan AP to the pupil plane PP, and the image of the field stop FS to the field plane FP. The imaging optics may comprise for example a lens, lenses, a mirror, mirrors, and/or diffractive optical components. For example, imaging optics may comprise one or two lenses.

The image forming optics of the light manipulation arrangement 104 may comprise one of more optically refractive and/or reflective components which may form a real image or a virtual image. The one of more optically refractive and/or reflective components may comprise at least one lens and/or mirror, which has a curved surface.

In an embodiment, the optical radiation source 102 may comprise one or more light emitting diodes (LED), organic light emitting diodes (OLED), lasers, any kind of light source capable of emitting at least partially visible light or the like for example.

Figure 20:
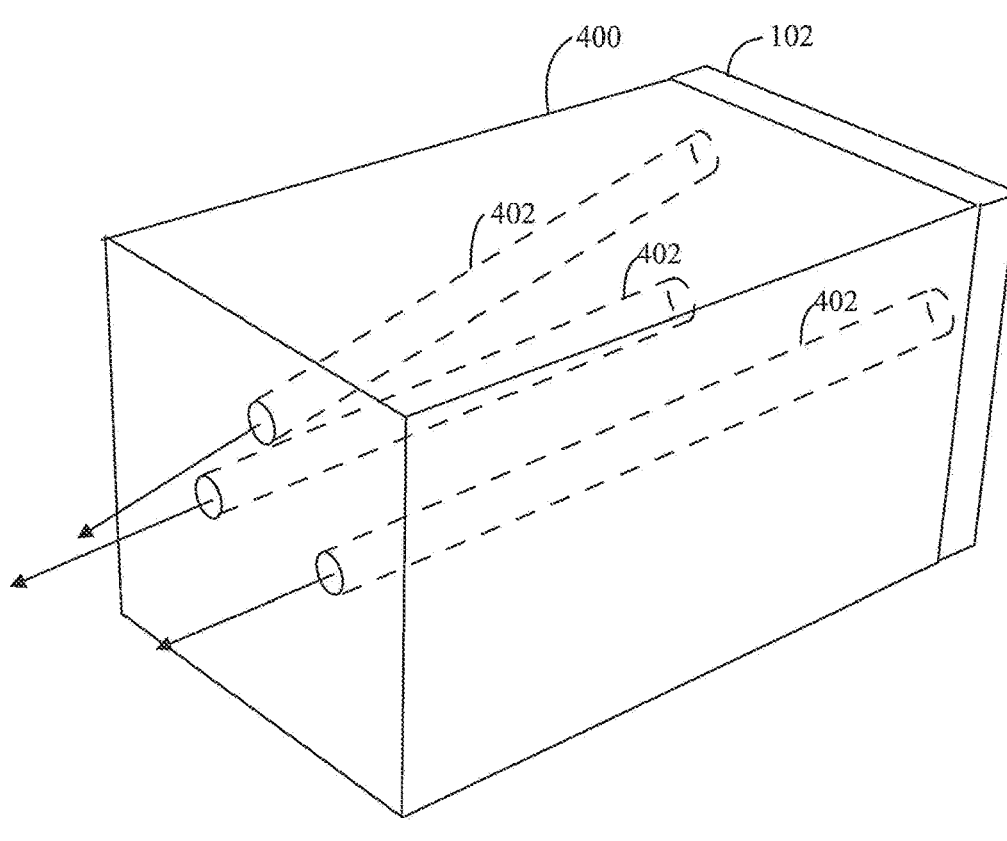
FIGS. 20 and 21 illustrate examples of a light manipulation arrangement, which forms beams light without image formation.
Figure 21:
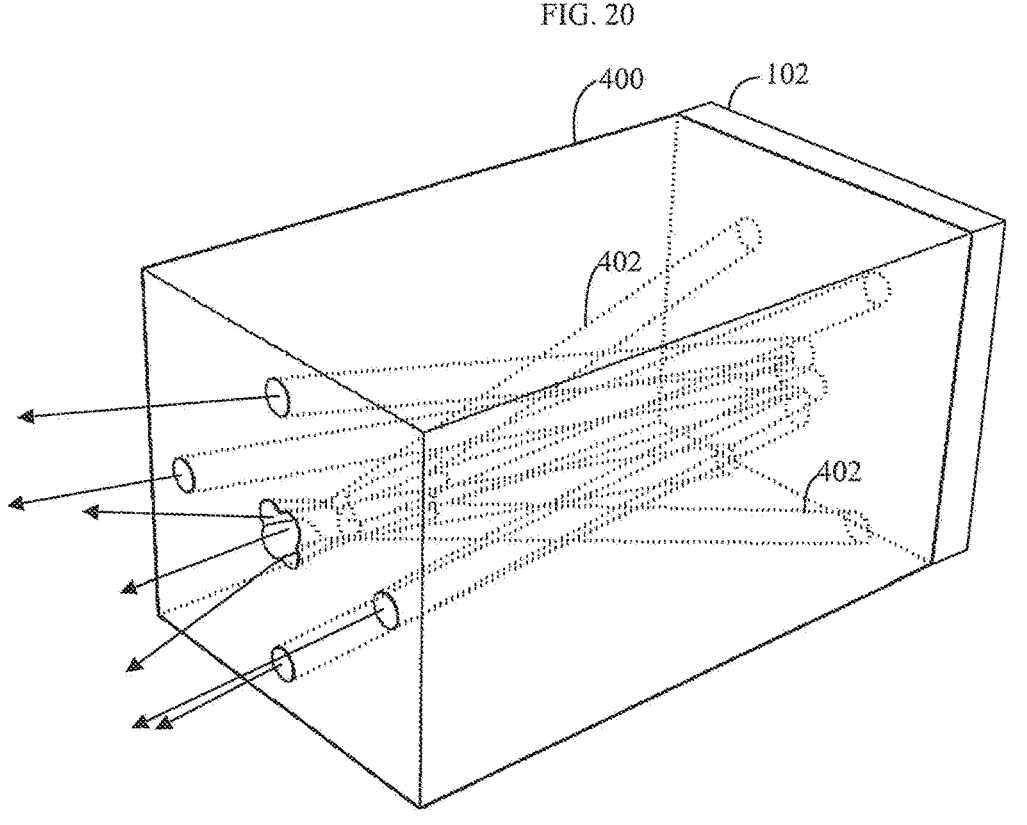

It is possible to form the light patterns 106 without image forming optical components (see FIGS. 20 and 21). Each light pattern 106 may be formed by shaping light beams emitted from the optical radiation source 102 by using apertures, which block unwanted light. In addition to or instead of apertures, many kinds of mechanical shapes or structures may be used to block the light, and form it to a desired shape. This may lead to a simple optical arrangement.

In an embodiment examples of which are illustrated in FIGS. 20 and 21, the light manipulation arrangement 104 may comprise at least one beam forming optical component 400, which forms separate beams of light directed to the pupil plane PP. The beams form the light patterns 106 that are directed through the pupil aperture 110. In the example of FIG. 20, all the beams are output from the ophthalmic examination instrument 100 in a converging manner.

In the example of FIG. 21, beams of light may represent the light patterns 106, some beams being directed in a diverging manner and some beams are directed in a converging manner.

In an embodiment, the at least one beam forming optical component 400 collimates the beams at least approximately. Then a cross section of the beams have about a constant area as a function of length of the beam between the ophthalmic examination apparatus 100 and pupil plane PP. A diameter of the beams may also have about a constant width as a function of length of the beam between the ophthalmic examination apparatus 100 and pupil plane PP.

In an embodiment, the light manipulation arrangement 104 may comprise a block of material that is opaque to visual radiation. The block of material may be similar to the beam forming component 400, see the examples of FIGS. 20 and 21. The block may have holes 402 which may form collimated beams of light that, in turn, may form the light patterns 106 in general and the at least one light pattern 108 that passes through pupil aperture 110 of the pupil plane PP.

Figures 22, 23, 24:
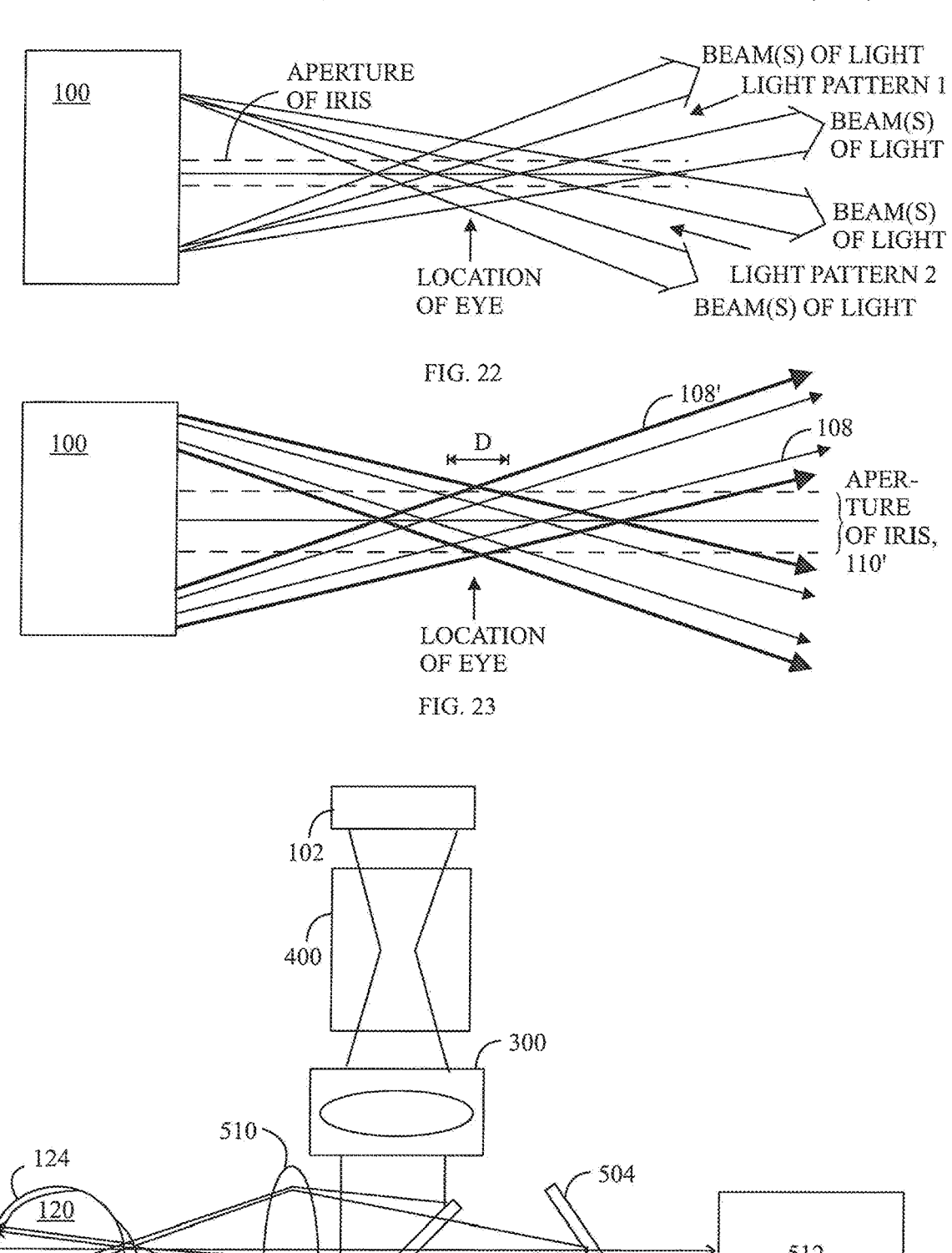
FIG. 22 illustrates an example of the at least one light pattern, which is formed by limiting light generated by the visual radiation source from entering the at least one light pattern.
FIG. 23 illustrates an example of light patterns for a large aperture of an iris of an eye.
FIG. 24 illustrates an example of an ophthalmic examination instrument.

In an embodiment, the light manipulation arrangement 104 may limit light generated by the visual radiation source 102 from entering the at least one light pattern 108, which are illustrated in FIG. 22 as light pattern 1 and light pattern 2, that passes through the pupil aperture 110 in the pupil plane PP. The arrows pointing out of the ophthalmic examination instrument 100 are beams of light.

In an embodiment, the light manipulation arrangement 104 may block or prevent the light from entering the at least one light pattern 108, i.e. light pattern 1 and light pattern 2, that passes through the pupil aperture 110 in the pupil plane PP. Then the light pattern 108 that passes through the pupil aperture 110 in the pupil plane PP may be lightless. Simultaneously, the light manipulation arrangement 104 may allow light propagation beside the at least one light pattern 108, the at least one light pattern 108 i.e. the light pattern 1 and the light pattern 2 passing through the pupil aperture 110 in the pupil plane PP. In this manner, the person can see a maximum of the at least one light pattern 108 that passes through the pupil aperture 110 in the pupil plane PP based on a minimum of light from the visual radiation source 102. That is, the at least one light pattern 108 that passes through the pupil aperture 110 in the pupil plane PP may be less illuminated than a volume directly adjacent to it. The volume directly adjacent to the at least one light pattern 108 that passes through the pupil aperture 110 in the pupil plane PP may be illuminated by the at least one light pattern 106 which does not pass through the pupil aperture 110 in the pupil plane PP. The eye 120 is according to this example in a proper examination position when the eye 120 receives least amount of illumination from the visual radiation source 102, for example. The guidance of the person is based on a fact that the person is instructed to search for such a minimum and it is easy to find such a position for the eye 120, because the minimum can only be found in a position where the examination of the eye 120 can be performed.

In an embodiment, the light manipulation arrangement 104 may pass light from the visual radiation source 102 optically therethrough in order to form the at least one light pattern 108 that also passes through the pupil aperture 110 in the pupil plane PP. In this example, the light manipulation arrangement 104 may limit light propagation beside the at least one light pattern 108 that passes through the pupil aperture 110 in the pupil plane PP. In an embodiment, the light manipulation arrangement 104 may block or prevent the light from entering a volume outside at least one light pattern 108 that passes through the pupil aperture 110 in the pupil plane PP. In this example, the person sees a maximum of the light patterns 108 that converges to the pupil aperture 110 in the pupil plane PP based on a maximum of light from the visual radiation source 102. The guidance of the person is based on a fact that the person is instructed to search for such a maximum and it is easy to find such a position for the eye 120, because the maximum can only be found in a position where the examination of the eye 120 can be performed. The maximum may refer to a maximum visibility of light from the visual radiation source 102. That is, the person tries to maximize the light intensity or coverage of the at least one pattern 108 on the retina 124.

In other words, during the guidance, the person finds such a position between his/her eye 120 and the ophthalmic examination instrument 100, where the iris of the eye 120 blocks or does not block the individual beams of the at least one light pattern 108 so that predetermined visibility of the beams is achieved to the retina 124.

In an embodiment examples of which are illustrated in FIGS. 12A to 18, the light manipulation arrangement 104 may direct a plurality of beams of light to the pupil plane PP, the plurality of beams of light forming the at least one light pattern 108 that passes through the pupil aperture 110 in the pupil plane PP. The plurality of beams of light may be distributed around the pupil center PO of the pupil aperture PP at the non-zero radial distances from the pupil center PO.

In an embodiment, one or more of the light patterns 106 may be represented in a non-blurred manner in the pupil plane PP of the ophthalmic examination apparatus 100. This means that the light patterns 106 do not need to have a sharp outer border.

In an embodiment, an optical power distribution of a cross section of one or more of the light patterns 106 in the pupil plane PP is non-flat. In an embodiment, an optical power distribution of a cross section of one or more of the light patterns 108 that pass through the pupil aperture 108 in the pupil plane PP is non-flat. This may result in a fact that the light patterns 106, 108 do not have a sharp outer border.

In an embodiment, one or more of the light patterns 106 are focused in the pupil plane PP of the ophthalmic examination apparatus 100. The focusing may be caused by the at least one image forming optical component 400 through which all light patterns 106 propagate to the pupil plane PP.

The at least one image forming optical component 400 may comprise one of more optically refractive and/or reflective components which may form a real image or a virtual image. The one of more optically refractive and/or reflective components may comprise at least one lens and/or mirror, which has a curved surface.

In an embodiment, one or more of the light patterns 106 are blurred in the pupil plane PP of the ophthalmic examination apparatus 100. These examples try to clarify the fact that the light patterns 106, 108 do not need to be seen sharp but emphasis more on a feature if the at least one light pattern 108 that passes through the pupil aperture 110 in the pupil plane PP is seen fully or partly.

In an embodiment an example of which is illustrated in FIG. 23, the light manipulation arrangement 104 may form two groups of light patterns 108 from the light of the visual radiation source 102 and direct at least one light pattern 108, 108' of each of the two light patterns 106, 106' through the pupil aperture 110. An angle of the convergence of the at least one light pattern 108 of a first group of the two groups of light patterns 106, 106' is different from an angle of the convergence of the at least one light pattern 108 of a second group of the two groups of light patterns 106, 106' in this example. This kind of arrangement makes it easier for a person who has a large aperture of the iris to find a proper position of his/her eye 12 more accurately with respect to the ophthalmic examination apparatus 100. As can be seen in FIG. 23, the large aperture of the iris allows the person to see all the light patterns 108 that pass through the pupil aperture 110 within a range D, but a range, which is illustrated in FIG. 23 with an vertical arrow and text location of eye, to see the light patterns 108' is much shorter thus making it possible to align the eye 120 much more accurately to a positon where the examination of the eye 120 can be made. The light patterns 108' pass through a larger pupil aperture 110'.

A diameter of the aperture 122 of the iris 126 may vary among the persons and due to ambient light, for example. That can be taken in account in the arrangement of the light patterns 106 such that in the pupil plane PP there are edges of light patterns in the whole region of the pupil aperture 110 where the iris 126 is allowed to vary, for example. Then the light patterns 108 that pass through the pupil aperture 110 either achieve their maximum or minimum brightness when the aperture 122 of the iris 126 allows or blocks their passage.

FIG. 24 illustrates an example of ophthalmic examination apparatus 100 such as a fundus camera with the alignment arrangement described above. The eye 120 is assumed to be a proper position for the examination.

The ophthalmic examination apparatus 100 has an illumination source 500, which in this example may direct light to a mirror 502 and its reflection to a first beam splitter 504. There may be a lens or lenses 506 between the mirror 502 and the first beam slitter 504. The first beam splitter 504 may then direct the light toward a second beam splitter 508, which may let the illumination light through via an objective 510 to the retina 124. The light reflects from the retina 124 and may travel through the objective 510 and the second beam splitter 504 to an image capturing unit 512 which may capture a still image or video of the retina 124. The image capturing may be performed using visible light or near-infrared light, for example. The objective lens 510 may image an aperture stop of the illumination approximately to the aperture 122 of the iris 126 of the eye 120, but laterally to a different position from the imaging channel in order to fulfil the Gullstrand's principle. The objective lens 510 may image the retina 124 to an intermediate image between the two beam splitters 504, 508, from which the image of the retina is further imaged by the image capturing unit 512.

The ophthalmic examination apparatus 100 may have a fixation target source 514, which may comprise one or more LEDs (Light Emitting Diode) illuminating one or more target field apertures (not particularly shown in FIG. 24). Light from the fixation target source 514 may be directed to the mirror 502 and its reflection to the first beam splitter 504. The first beam splitter 504 may then direct the light toward the second beam splitter 508, which may let the illumination light through via the objective 510 to the retina 124. When the person sees the target he/she may turn his/head and/or his/her eye 120 toward the target. Because the target field apertures are imaged approximately to the retina 124, i.e. they may form the visible target spots to the person's field-of-view. The target aperture stop may be imaged to the pupil plane PP approximately between the imaging and illumination beams.

The ophthalmic examination instrument 100 has the at least one visual radiation source 102, and the light manipulation arrangement 104, which forms a number of light patterns 106 which include the at least one light pattern 108 (illustrated by the envelope beam) that passes through the pupil aperture 110 that has the waist W at the pupil aperture 110. The light patterns 106 may propagate to the image forming optical component 300, then to the second beam splitter 508 and the objective lens 510. From the objective lens 510 the light patterns 108 that pass through the pupil aperture 110 may continue to the retina 124 of the eye 120. The waist W of the light patterns 108 makes it possible for the light patterns 108 to pass through the pupil aperture 110.

The light manipulation arrangement 104 may comprise, for example, the parts shown in FIGS. 20, 21, which are blocks of substantially non-transparent material comprising holes 402, which may form separate beams of light.

For the eye alignment purpose, only the visibility of the light patterns 106 is important, and the light patterns 106 do not need to be in focus. That is why the method may also work well with near- or far-sightedness, age-related vision changes, or with other eye issues.

On the other hand, the light patterns 106 may be used for focusing the eye 120 in such ophthalmic examination instruments 100, where the eye focus is critical. For example, in use of a fundus camera, the illumination field stop may be arranged to contain image, which is imaged to the field plane (FP) by the image forming component 300. The image may comprise a recognizable figure with contrast so that the eye 120 of the person may try to focus to it. The field plane (FP) may be arranged to be at the same focus position in respect to the eye than the camera sensor of the image capturing unit 512.

If the eye 120 succeeds focusing the pattern 106, the retina 124 of the eye 120 is also focused on the sensor of the image capturing unit 512. The person may be provided a user interface, a knob or the like, which can be used to adjust the focus of the ophthalmic examination instruments 100 (i.e. simultaneously the focus of the light patterns 106 and the sensor) so that he/she can get a sharp image in case that his/her eye 120 does not have enough focusing power.

As already described in association with FIG. 24, the person's eye 120 may simultaneously, or successively, see both a fixation target and the light patterns 106. In order to distinct between them, the fixation target may be in different color, and/or be bright enough, or may be flickering, in an embodiment.

Figure 25:
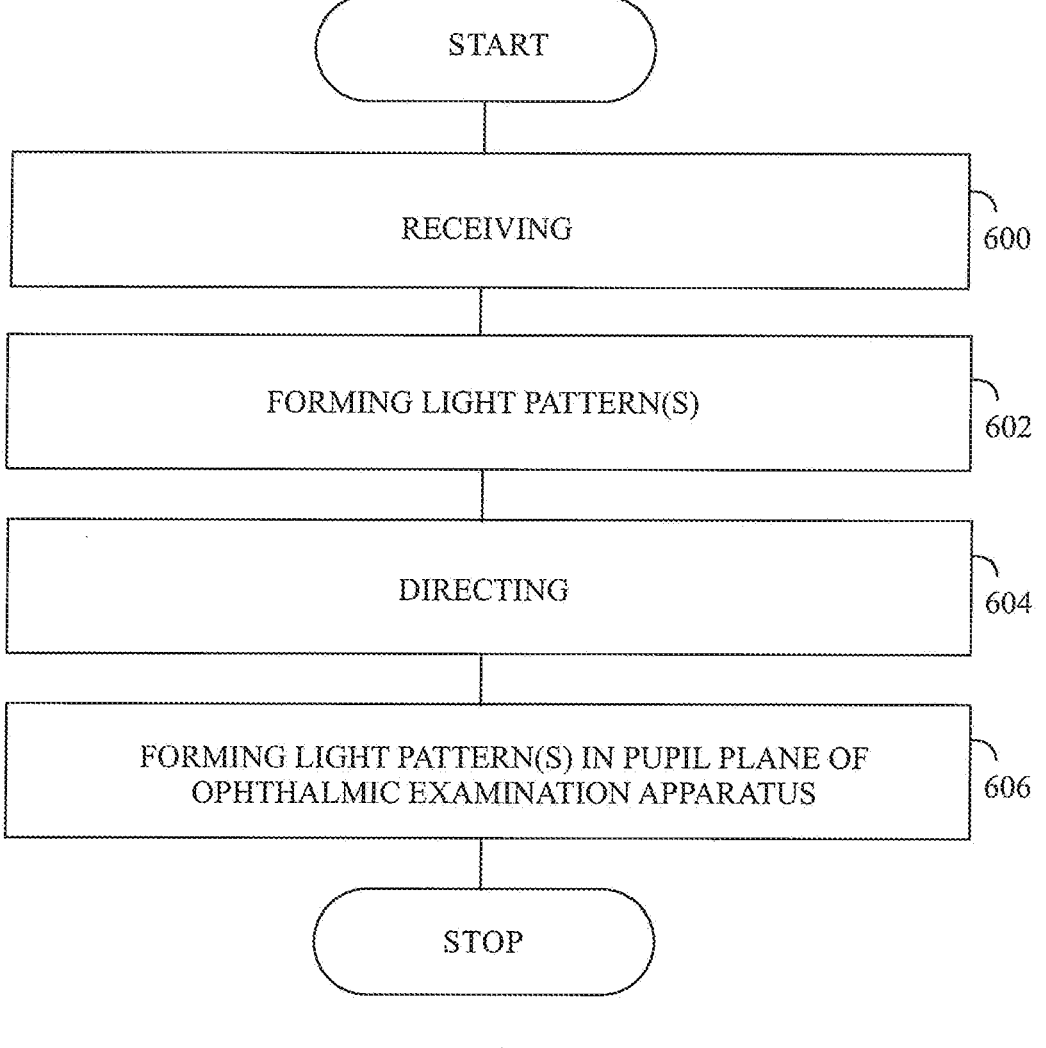
FIG. 25 illustrates of an example of a flow chart of an alignment method.

FIG. 25 is a flow chart of the alignment method, where a light manipulation arrangement 104 of the ophthalmic examination apparatus 100 performs the following steps. In step 600, the light manipulation arrangement 104 light receives from a visible radiation source 102. In step 602, light patterns 106 of the light are formed. In step 604, at least one light pattern 108 of the light patterns 106 is directed in a converging manner toward an pupil aperture PO of the ophthalmic examination apparatus 100. In step 606, the at least one light pattern 108 is formed at a non-zero radial distance from a pupil center PO of the pupil aperture 110 in a pupil plane PP of the ophthalmic examination apparatus 100 such that a waist W of the at least one light pattern 108 is located at the pupil plane PP in order to provide a person with guidance for overlapping an aperture of an iris 126 of his/her eye 120 with the pupil aperture 110 in the pupil plane PP.

As a conclusion, the set of light patterns 108 that pass through the pupil aperture 110 of the pupil plane PP may be arranged such that a maximum visibility of the light patterns 108 to the person's eye indicates the proper eye position the envelope 700 has the waist W close or at the pupil plane PP such that when the eye 120 is aligned at the desired position and orientation with the ophthalmic examination instrument 100, the waist W is centered at the aperture 122 of the iris 126 of the eye 120 when the eye 120 is at the desired position, the envelope 700 may pass the aperture 122 of the iris 126 of the eye 120 with least obscured way, and so the at least one light pattern 108 as a whole may travel to the retina 124 with least obscured way providing visibility of the at least one light pattern to the person's eye 120 if the eye 120 is decentered in x- or y-dimensions, or has translated along z-axis (axial shift) with respect to the desired position, the iris 126 of the eye 120 may block at least part of the envelope 700 and underlying at least one light pattern 108, indicating to the person that the alignment needs to be adjusted to a direction which reduces blocking the projection of the envelope 700 to different planes parallel to the eye axis EA may have waists at different positions from the waist W of the envelope 700 as whole.

The light patterns 106 may also operate as the fixation target(s). That may be implemented for example such that the at least one light pattern that passes through the aperture pupil 110 as a whole is sufficiently small such that when the person sees any part of it, the eye 120 is guided in to correct its direction toward it with sufficient accuracy.

There are ophthalmic instruments, such as fundus cameras, which typically require accurate alignment of the iris 126 of the eye 120 to the instrument. An advantage of what is taught in this document is that the alignment is done by using the same, i.e. iris 126 of the eye 120, and so the alignment becomes inherently robust with respect to eye imaging errors, or even to the gaze direction of the eye 120. For example, when applied to fundus cameras, the same set of light paths 108 may be used when imaging different parts of the retina 124.

What is described above may be suitable for any kind of ophthalmic examination instrument 100 which needs to be aligned precisely with the eye 120, the ophthalmic examination instrument 100 being such as a fundus camera or an ophthalmic treatment instruments, for example.

As the described, the alignment allows the person to perform the precise alignment of the instrument to his eye, the other person may not be needed for using the ophthalmic examination instrument 100. The person may move his eye 120 with respect to the ophthalmic examination instrument 100, or move the optics of the ophthalmic examination instrument 100 with respect to the eye 120, or both. The ophthalmic examination instrument 100 may have a user interface which enables the person to perform the alignment precisely by motorized means for example. The ophthalmic examination instrument 100 may have means to move the desired eye position (i.e. pupil plane PP of the ophthalmic examination instrument 100) by using the user interface.

The user of the ophthalmic examination instrument 100, i.e. operator, may be the person whose eye 120 is examined. The operator may not necessarily be a human being, but the ophthalmic examination instrument 100 may be an automatic or autonomous device where the operator is replaced by automation. The operator may also not be present next to the ophthalmic examination instrument 100, but may be in different location and operate the ophthalmic examination instrument 100 by a remote access.

The alignment of the ophthalmic examination apparatus 100 and the eye 120 is advantageous and may be observed for example as:

improved alignment accuracy faster alignment suitability for patient operated and/or autonomous apparatus improved patient experience.

It will be obvious to a person skilled in the art that, as technology advances, the inventive concept can be implemented in various ways. The invention and its embodiments are not limited to the example embodiments described above but may vary within the scope of the claims.

The invention claimed is:

1. An ophthalmic examination apparatus of fundus of an eye, wherein the ophthalmic examination apparatus comprises:

at least one visual radiation source and a light manipulation arrangement, which is configured to receive light from the visible radiation source, and form light patterns from the light and direct at least four light patterns of the light patterns within an envelope, the light patterns having subareas on the pupil plane and the field plane, wherein:

each of the at least four light patterns is generated by a plurality of distinct beams directed toward and through the pupil aperture, the plurality of beams having a beam waist located substantially at the pupil plane such that the envelope of the beams forms a minimum cross-section at the pupil plane corresponding to the pupil aperture and avoids substantial illumination of the iris when the eye is correctly aligned, the envelope being defined as a convex hull, in planes parallel to the pupil plane, that encloses cross-sections of the plurality of beams forming the light patterns, the light manipulation arrangement is configured to form a first pair of the at least four light patterns and a second pair of the at least four light patterns, the first light patterns and the second light patterns having opposite signs of an angle between lines that are configured to go between centroids of beams of the light patterns in the pupil plane and the field plane, said opposite signs of convergence angle correspond to beams that intersect the pupil plane from geometrically different sides along the z-axis, producing z-axis alignment cues based on sector-specific iris occlusion rather than focus sharpness, and the light manipulation arrangement is configured to locate the at least four light patterns at separate sectors of the pupil aperture and at a non-zero radial distance from a pupil center of the pupil aperture, wherein each sector contains a light pattern confined to a distinct radial sub-region such that misalignment in x, y, or z directions causes sector-specific iris blocking of corresponding beams, resulting in disappearance of one or more light patterns irrespective of focus based on the angles such that the beam waist of the light patterns is located at the pupil plane, and configured such that the visibility of all sector-specific light patterns is maximized only when the aperture of the iris geometrically overlaps the pupil aperture, wherein iris occlusion of any beam results in partial or full loss of the corresponding sector-specific light pattern on the retina, thereby providingx-, y-, and z-axis alignment guidance without relying on visual acuity or image sharpness.

2. The ophthalmic examination apparatus of claim 1, wherein the light manipulation arrangement comprises at least one image forming optical component, which is configured to form an image of an aperture plane of the at least one visual radiation source in the pupil plane, the aperture plane comprising the light patterns.

3. The ophthalmic examination apparatus of claim 2, wherein the at least one image forming optical component is configured to form an image of an illumination field stop to a field plane.

4. The ophthalmic examination apparatus of claim 1, wherein the light manipulation arrangement comprises at least one beam forming optical component, which is configured to form separate beams of light directed to the pupil plane, the beams forming the light patterns.

5. The ophthalmic examination apparatus of claim 1, wherein the light manipulation arrangement comprises a block of material that is opaque to visual radiation, and the block has holes which are configured to form beams of light that are configured to form the at least one light pattern that is configured to pass through the pupil aperture in a pupil plane.

6. The ophthalmic examination apparatus of claim 1, wherein the light manipulation arrangement is configured to limit light from the visual radiation source from entering the at least one light pattern that is configured to converge to the pupil aperture in a pupil plane, and allow light propagation beside the at least one light pattern that is configured to converge to the pupil aperture in a pupil plane, and cause the person to see a maximum of the at least one light pattern that is configured to pass through the pupil aperture in a pupil plane based on a minimum of light from the visual radiation source.

7. The ophthalmic examination apparatus of claim 1, wherein the light manipulation arrangement is configured to pass light from the visual radiation source optically therethrough in order to form the at least one light pattern that is configured to converge to the pupil aperture in a pupil plane and limit light propagation beside the at least one light pattern that is configured to pass through the pupil aperture in a pupil plane in order to cause the person to see a maximum of the light patterns based on a maximum of light from the visual radiation source.

8. The ophthalmic examination apparatus of claim 1, wherein the light manipulation arrangement is configured to direct a plurality of beams of light to the pupil plane, the plurality of beams of light being configured to form the at least one light pattern that is configured to pass through the pupil aperture in a pupil plane, and the plurality of beams of light being distributed around the pupil center of the pupil aperture at the non-zero radial distances from the pupil center.

9. The ophthalmic examination apparatus of claim 1, wherein one or more of the light patterns are represented in a non-blurred manner in the pupil plane of the ophthalmic examination apparatus.

10. The ophthalmic examination apparatus of claim 1, wherein one or more of the light patterns are blurred in the pupil plane of the ophthalmic examination apparatus.

11. The ophthalmic examination apparatus of claim 1, wherein an optical power distribution in a plane of a cross section of one or more of the light patterns in the pupil plane is non-flat.

12. The ophthalmic examination apparatus of claim 1, wherein the light manipulation arrangement is configured to form two groups of light patterns from the light and direct at least one light pattern of each of the two light patterns in a converging manner to the pupil aperture, an angle of the convergence of the at least one light pattern of a first group of the two groups of light patterns being different from an angle of the convergence of the at least one light pattern of a second group of the two groups of light patterns.

\* \* \* \* \*